United States Patent
Oldani et al.

(10) Patent No.: US 9,944,571 B2
(45) Date of Patent: Apr. 17, 2018

(54) ONE-POT PROCESS USING HETEROGENEOUS CATALYST

(71) Applicant: SOLVAY SPECIALTY POLYMERS ITALY S.P.A., Bollate (IT)

(72) Inventors: Claudio Oldani, Parabiago (IT); Luca Merlo, Montorfano (IT); Pierluigi Barbaro, Sesto Fiorentino (IT); Carmen Moreno-Marrodan, Sesto Fiorentino (IT); Francesca Liguori, Prato (IT)

(73) Assignee: SOLVAY SPECIALTY POLYMERS ITALY S.P.A., Bollate (IT)

( * ) Notice: Subject to any disclaimer, the term of this patent is extended or adjusted under 35 U.S.C. 154(b) by 0 days.

(21) Appl. No.: 15/528,338

(22) PCT Filed: Nov. 16, 2015

(86) PCT No.: PCT/EP2015/076646
§ 371 (c)(1),
(2) Date: May 19, 2017

(87) PCT Pub. No.: WO2016/079036
PCT Pub. Date: May 26, 2016

(65) Prior Publication Data
US 2017/0320789 A1 Nov. 9, 2017

(30) Foreign Application Priority Data

Nov. 19, 2014 (EP) ..................... 14193925

(51) Int. Cl.
| | | |
|---|---|---|
| C07B 31/00 | (2006.01) | |
| B01J 31/28 | (2006.01) | |
| B01J 31/06 | (2006.01) | |
| C07D 307/33 | (2006.01) | |
| C07C 29/17 | (2006.01) | |

(52) U.S. Cl.
CPC .............. *C07B 31/00* (2013.01); *B01J 31/06* (2013.01); *B01J 31/28* (2013.01); *C07C 29/175* (2013.01); *C07D 307/33* (2013.01); *B01J 2231/52* (2013.01); *B01J 2231/643* (2013.01); *C07C 2601/14* (2017.05)

(58) Field of Classification Search
CPC ..................................................... C07B 31/00
USPC ......................................................... 549/326
See application file for complete search history.

(56) References Cited

U.S. PATENT DOCUMENTS

| | | |
|---|---|---|
| 2,786,852 A | 3/1957 | Dunlop et al. |
| 4,420,622 A | 12/1983 | Cornelis et al. |
| 4,940,525 A | 7/1990 | Ezzell et al. |
| 5,883,266 A | 3/1999 | Elliott et al. |
| 2004/0254384 A1 | 12/2004 | Manzer et al. |
| 2005/0136309 A1 | 6/2005 | Masel et al. |
| 2008/0003479 A1 | 1/2008 | Yoon et al. |
| 2009/0075139 A1 | 3/2009 | Kucernak et al. |
| 2012/0077671 A1 | 3/2012 | Starz et al. |

FOREIGN PATENT DOCUMENTS

| | | |
|---|---|---|
| CN | 101722049 A | 6/2010 |
| EP | 1172382 A | 1/2002 |
| EP | 1238999 A | 9/2002 |
| EP | 1239000 A | 9/2002 |
| EP | 1323751 A | 7/2003 |
| KR | 101285121 B1 | 7/2013 |
| WO | 13158272 A1 | 10/2013 |
| WO | 13162499 A1 | 10/2013 |
| WO | 14033204 A1 | 3/2014 |

OTHER PUBLICATIONS

Yashtulov, N. A., et al., "Metal-polymer electrocatalyst based on palladium nanoparticles", Vestnik Mitkht, 2011, 6(4), p. 54-58. (With English Language Abstract).
Yashtulov, N. A., et al., "Catalytic Activity of Polymer-Palladium Metal Nanocomposites in Oxygen Reduction and Hydrogen Oxidation Reactions", Kinetics and Catalysis, 2013, 54(3), p. 322-325.
Wang, Ting, et al., "Electrodeposition of monodispersed metal nanoparticles in a Nafion film: Towards highly active nanocatalysts", Electrochemistry Communications, 2008, 10(5), p. 814-817.
Moreno-Marrodan, Carmen, et al. "Energy efficient continuous production of [gamma]-valerolactone by bifunctional metal/acid catalysis in one pot", Green Chemistry, 2014, vol. 16,Nr.7, p. 3434.

*Primary Examiner* — Taofiq A Solola (57) ABSTRACT

The present invention relates to a process for the one-pot hydrogenation and dehydration or isomerization of an organic compound, and to a catalyst composition for this process comprising transition metal particles having particle size below 50 nm supported on a material comprising at least one fluorinated polymer (P), wherein polymer (P) bears —$SO_2X$ functional groups, X being selected from X' and OM, X' being selected from the groups consisting of F, Cl, Br and I; and M being selected from the group consisting of H, and alkaline metal and $NH_4$.

19 Claims, 2 Drawing Sheets

ONE-POT PROCESS USING HETEROGENEOUS CATALYST

CROSS-REFERENCE TO RELATED APPLICATION

This application is a U.S. national stage entry under 35 U.S.C. § 371 of International Application No. PCT/EP2015/076646 filed Nov. 16, 2015, which claims priority to European application No. 14193925.6 filed on Nov. 19, 2014. The entire contents of these applications are explicitly incorporated herein by this reference.

TECHNICAL FIELD

The present invention relates to a process for the one-pot hydrogenation and dehydration or isomerization of an organic compound.

BACKGROUND ART

Several important market products, fine or commodity chemicals, are currently produced using step-by-step processes, which require separate reaction units, purification steps and often drastic reaction conditions, with serious economic and environmental drawbacks. The demand is still felt for processes that are easily applicable on industrial scale and that enable one-pot cascade/tandem reaction sequences to provide faster, more environmentally friendly and cost-effective overall transformation of basic substrates into more complex chemicals.

Levulinic acid is a well-known product of hexose acid hydrolysis, and is inexpensively obtained from cellulose feedstocks. Consequently, it is an attractive starting material in producing useful 5-carbon compounds, such as methyl-tetrahydrofuran and derivatives and 5-methyl-dihydro-furan-2-one, also known as gamma-valerolactone.

U.S. Pat. No. 2,786,852 A (QUAKER OATS COMPANY) 26 Mar. 1957 discloses production of 5-methyl-dihydro-furan-2-one from levulinic acid in vaporized form, suspended in a stream of hydrogen gas, using a reduced copper oxide catalyst at a temperature from 175 to 250° C.

U.S. Pat. No. 5,883,266 A (BATTELLE MEMORIAL INSTITUTE) 16 Mar. 1999 discloses the use of a bimetal catalyst to prepare a variety of products from levulinic acid including 5-methyl-dihydro-furan-2-one at a reaction temperature of 200° C. or 250° C. at an operating pressure of 100 atm.

U.S. Pat. No. 4,420,622 A (STAMICARBON) 13 Dec. 1983 is relative to the preparation of 5-alkyl-butyrolactones using $C_8$ hydrocarbon levulinate esters, with side-chain alkyl substituents of up to 4 carbon atoms as starting material, with the reaction being conducted with hydrogen at a temperature of from 150 to 325° C., in the gas phase, and in the presence of a hydrogenation catalyst composed of metals of Group VIII or Group Ib of the Periodic Table.

U.S. 20040254384 A (DU PONT) 16 Dec. 2004 discloses the transformation of levulinic acid to gamma-valerolactone using a metal catalyst in the presence of a superfluid solvent.

Aim of the present invention is to provide a method for the conversion of readily available starting materials, such as levulinic acid, into advanced intermediates, such as gamma-valerolactone and its derivatives, under relatively mild conditions. Another object of the present invention is to provide a process for such transformations that can be easily scaled to industrial productions and that is cost-effective and environmentally friendly.

SUMMARY OF INVENTION

These aims are solved by the present invention by means of a process for the one-pot hydrogenation and acid-catalysed isomerisation or dehydration of a substrate (I) containing at least a C=C, a C=O, an acetal, a 1,2-diol or a hemiacetal moiety to obtain a product (II), wherein said process comprises the step of reacting the substrate with hydrogen ($H_2$) in the presence of a catalyst (III), said catalyst comprising transition metal particles having particle size below 50 nm supported on a material comprising at least one fluorinated polymer (P), wherein polymer (P) bears —$SO_2X$ functional groups, X being selected from X' and OM, X' being selected from the group consisting of F, Cl, Br, and I; and M being selected from the group consisting of H, an alkaline metal and $NH_4$.

The inventors found that the one-pot process of the invention provides advanced intermediates in high yields with little or no side products and the solid catalyst can be easily recovered and re-used in several cycles without loss of catalytic activity.

Unlike the methods of prior art, high catalyst productivities are obtained with the one-pot process of the present invention without the addition of strong acids, resulting in a cleaner and more environmentally-friendly process and a longer catalyst lifecycle.

In the methods of prior art, extra downstream processing steps are needed to remove the metal leached from the catalyst and/or to purify the reaction products, harsh reaction conditions (high temperature and hydrogen pressure, toxic reagents). Notably, it was found that metal atoms supported on the fluorinated polymer are not released into the reaction medium in the process of the present invention, hence no purification steps are necessary.

DESCRIPTION OF EMBODIMENTS

Figure 1:
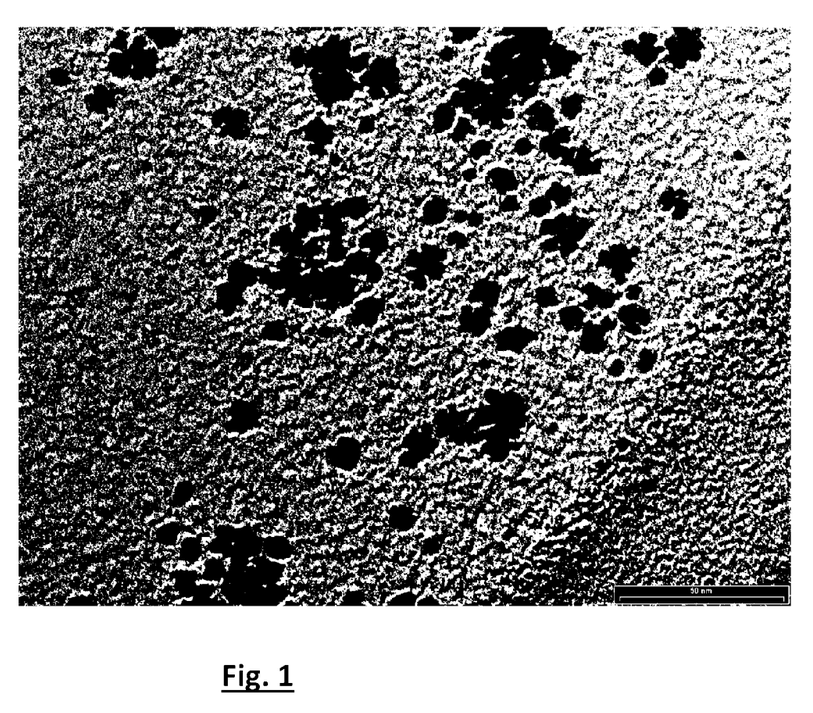
FIG. 1 shows a TEM image of the composition according to the present invention (Metal=Ru, average D50 particle size=3.4 micrometers, support=Aquivion® PFSA)
Figure 2:
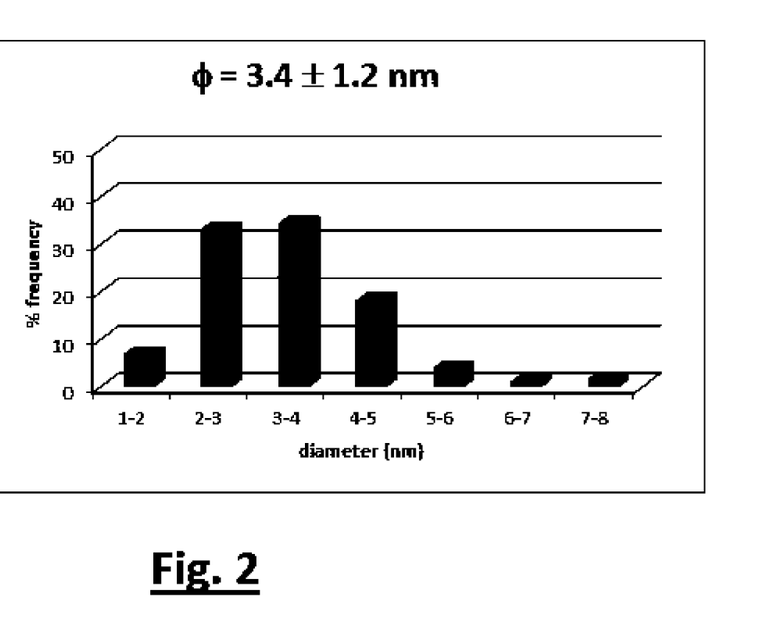
FIG. 2 shows the particle size distribution of the composition as shown in FIG. 1.

In one embodiment, the present invention provides a one-pot process for hydrogenation and dehydration/isomerization of a substrate in the presence of a bifunctional catalyst.

As used herein, "one-pot" indicates a process wherein two or more chemical transformations are carried out starting from a substrate in a single reactor unit, without isolation or separation of any reaction intermediate.

Said catalyst comprises active metal particles on a support comprising a least one fluorinated polymer (P) bearing —$SO_2X$ functional groups, wherein X is as defined above.

Fluorinated polymers containing sulfonic acid ion exchange groups (also known as ionomers or PFSA) have found widespread use in the manufacture of electrolyte membranes for electrochemical devices such as electrolysis cells and fuel cells, mainly due to their ion-conducting properties. Notable examples are, for instance, proton exchange membrane (PEM) fuel cells which employ hydrogen as the fuel and oxygen or air as the oxidant.

The terms "fluorinated polymer" or "fluoropolymer" as used herein refer to compounds (e.g. polymers, monomers etc.) that are either totally or partially fluorinated, i.e.

wherein all or only a part of the hydrogen atoms of an hydrocarbon structure have been replaced by fluorine atoms. Preferably, the term "fluorinated" refers to compounds that contain a higher proportion of fluorine atoms than hydrogen atoms, more preferably to compounds that are totally free of hydrogen atoms, i.e. wherein all the hydrogen atoms have been replaced by fluorine atoms (perfluoro compounds).

Suitable fluorinated polymers comprising —$SO_2X'$ functional groups are those polymers comprising recurring units deriving from at least one ethylenically unsaturated fluorinated monomer containing at least one —$SO_2X'$ functional group (monomer (A) as hereinafter defined) and recurring units deriving from at least one ethylenically unsaturated fluorinated monomer (monomer (B) as hereinafter defined).

The phrase "at least one monomer" is used herein with reference to monomers of both type (A) and (B) to indicate that one or more than one monomer of each type can be present in the polymer. Hereinafter the term monomer will be used to refer to both one and more than one monomer of a given type.

Non-limiting examples of suitable monomers (A) are:
sulfonyl halide fluoroolefins of formula: $CF_2=CF(CF_2)_p SO_2X'$ wherein p is an integer between 0 and 10, preferably between 1 and 6, more preferably p is equal to 2 or 3, and wherein preferably X'=F;
sulfonyl halide fluorovinylethers of formula: $CF_2=CF-O-(CF_2)_mSO_2X'$ wherein m is an integer between 1 and 10, preferably between 1 and 6, more preferably between 2 and 4, even more preferably m equals 2, and wherein preferably X'=F;
sulfonyl halide fluoroalkoxyvinylethers of formula: $CF_2=CF-(OCF_2CF(R_{F1}))_w-O-CF_2(CF(R_{F2}))_y SO_2X'$
wherein w is an integer between 0 and 2, $R_{FS}$ and $R_{F2}$, equal or different from each other, are independently F, Cl or a $C_1$-$C_{10}$ fluoroalkyl group, optionally substituted with one or more ether oxygen atom, y is an integer between 0 and 6, preferably w is 1, $R_{F1}$ is —$CF_3$, y is 1 and $R_{F2}$ is F, and wherein preferably X'=F;
sulfonyl halide aromatic fluoroolefins of formula $CF_2=CF-Ar-SO_2X'$ wherein Ar is a $C_5$-$C_{15}$ aromatic or heteroaromatic substituent, and wherein preferably X'=F.

Preferably the monomer (A) is selected from the group of the sulfonyl fluorides, i.e. wherein X'=F. More preferably monomer (A) is selected from the group of the fluorovinylethers of formula $CF_2=CF-O-(CF_2)_m-SO_2F$, wherein m is an integer between 1 and 6, preferably between 2 and 4. Even more preferably the monomer (A) is $CF_2=CFOCF_2CF_2-SO_2F$ (perfluoro-5-sulfonylfluoride-3-oxa-1-pentene).

Non-limiting examples of suitable ethylenically unsaturated fluorinated monomers of type (B) are:
$C_2$-$C_8$ fluoroolefins, such as tetrafluoroethylene, pentafluoropropylene, hexafluoropropylene, and hexafluoroisobutylene; vinylidene fluoride;
$C_2$-$C_8$ chloro- and/or bromo- and/or iodo-fluoroolefins, such as chlorotrifluoroethylene and bromotrifluoroethylene; fluoroalkylvinylethers of formula $CF_2=CFOR_{f1}$, wherein $R_{f1}$ is a $C_1$-$C_6$ fluoroalkyl, e.g. —$CF_3$, —$C_2F_5$, —$C_3F_7$; fluoro-oxyalkylvinylethers of formula $CF_2=CFOR_{O1}$, wherein $R_{O1}$ is a $C_1$-$C_{12}$ fluoro-oxyalkyl having one or more ether groups, for example perfluoro-2-propoxy-propyl; fluoroalkylmethoxy-vinylethers of formula $CF_2=CFOCF_2OR_{f2}$ in which $R_{f2}$ is a $C_1$-$C_6$ fluoroalkyl, e.g. —$CF_3$, —$C_2F_5$, —$C_3F_7$ or a $C_1$-$C_6$ fluorooxyalkyl having one or more ether groups, like —$C_2F_5$—O—$CF_3$; fluorodioxoles, of formula:

wherein each of $R_{f3}$, $R_{f4}$, $R_{f5}$, $R_{f6}$, equal or different from each other, is independently a fluorine atom, a $C_1$-$C_6$ fluoro(halo)fluoroalkyl, optionally comprising one or more oxygen atom, e.g. —$CF_3$, —$C_2F_5$, —$C_3F_7$, —$OCF_3$, —$OCF_2CF_2OCF_3$.

Preferably monomer (B) is selected among:
$C_3$-$C_8$ fluoroolefins, preferably tetrafluoroethylene and/or hexafluoropropylene;
chloro- and/or bromo- and/or iodo-$C_2$-$C_6$ fluoroolefins, like chlorotrifluoroethylene and/or bromotrifluoroethylene;
fluoroalkylvinylethers of formula $CF_2=CFOR_{f1}$ in which $R_{f1}$ is a $C_1$-$C_6$ fluoroalkyl, e.g. —$CF_3$, —$O_2F_5$, —$O_3F_7$;
fluoro-oxyalkylvinylethers of formula $CF_2=CFOR_{O1}$, in which $R_{O1}$ is a $C_1$-$C_{12}$ fluorooxyalkyl having one or more ether groups, like perfluoro-2-propoxy-propyl group.

Most preferably monomer (B) is tetrafluoroethylene.

The composition in the process of the invention may comprise the at least one fluorinated polymer in the neutral form, wherein the expression "neutral form" indicates that in the —$SO_2X$ functional groups X is X' and X' is selected from the group consisting of F, Cl, Br, I. Preferably X' is selected from F or Cl. More preferably X' is F.

Alternatively, the composition may comprise the at least one fluorinated polymer in the ionic (acid or salified) form, wherein the expression "ionic form" indicates that, in the —$SO_2X$ functional groups, X is OZ and Z is selected from the group consisting of H, alkaline metals, $NH_4$.

For the avoidance of doubt, the term "alkaline metal" is hereby intended to denote the following metals: Li, Na, K, Rb, Cs. Preferably the alkaline metal is selected from Li, Na, K.

Fluorinated polymers comprising —$SO_3Z$ functional groups are typically prepared from fluorinated polymers comprising —$SO_2X'$ functional groups, preferably —$SO_2F$ functional groups, by methods known in the art. The fluorinated polymer can be obtained in its salified form, i.e. wherein Z is a cation selected from the group consisting of $NH_4$ and alkaline metals, by treatment of the corresponding polymer comprising —$SO_2X'$ functional groups, typically —$SO_2F$ functional groups, with a strong base (e.g. NaOH, KOH). The fluorinated polymer can be obtained in its acid form, i.e. wherein Z is H, by treatment of the corresponding salified form of the polymer with a concentrated acid solution.

The fluorinated polymer comprising —$SO_2X'$ functional groups may be prepared by any polymerization process known in the art. Suitable processes for the preparation of such polymers are for instance those described in U.S. Pat. No. 4,940,525 A (THE DOW CHEMICAL COMPANY) 10 Jul. 1990, EP 1323751 A (SOLVAY SOLEXIS SPA) 2 Jul. 2003 and EP 1172382 A (SOLVAY SOLEXIS SPA) 16 Nov. 2002.

The fluorinated polymer to be used in the method of the invention can also be obtained by cross-linking of the sulfonic fluorinated polymer, the cross-linking involving the backbone of the polymer. The fluoropolymers can be of any type, also suitable both for use as ion-conducting membranes in electrochemical cells as well as filtration membranes.

The use of cross-linking to improve the physical resistance of catalysts made from fluorinated polymers containing sulfonic acid functional groups has been previously disclosed. For instance, EP 1238999 A (SOLVAY SOLEXIS SPA) 11 Sep. 2002 and EP 1239000 A (SOLVAY SOLEXIS SPA) 11 Sep. 2002 disclose hydrophilic membranes comprising cross-linkable sulfonic fluorinated polymers comprising: monomeric units deriving from tetrafluoroethylene, fluorinated monomeric units containing sulfonyl groups —$SO_2F$, and from 0.01% to 5% by moles of monomeric units deriving from a bis-olefin of formula (I): $R_1R_2C=CH-(CF_2)m-CH=CR_5R_6$ (wherein m=2-10, $R_1$, $R_2$, $R_5$, $R_6$, equal to or different from each other, are H or $C_1$-$C_5$ alkyl groups).

Non-limitative examples of fluorinated polymers suitable for use in the process of the invention are the commercial products Nafion® (Du Pont) and Aquivion® PFSA (Solvay). Those polymers are thermally, mechanically and chemically resistant under the reaction conditions of the present invention, while showing significant swelling volume in the used solvents, and comprise a fluorinated polymeric backbone and strongly acidic functional groups.

Nafion® PFSAs are fluoropolymers produced by DuPont and containing sulfonate groups on a tetrafluoroethylene backbone. Nafion® PFSAs are part of class of synthetic polymers with ionic properties, which are called ionomers.

Nafion® PFSAs are copolymers of TFE and perfluoro-3,6-dioxa-4-methyl-7-octenesulfonic acid, that are referred to as "long-side chain ionomers".

Aquivion® PFSAs are fluoropolymers produced by Solvay Specialty Polymers Italy, S.p.A. and containing sulfonate groups on a tetrafluoroethylene backbone, and are based on Short Side Chain (SSC) copolymer of Tetrafluoroethylene and a linear Sulfonyl Fluoride Vinyl Ether (SFVE), namely $F_2C=CF-O-CF_2CF_2-SO_2F$, of low molecular weight. The PFSA ionomer dispersions contain Aquivion® PFSA in its acid form (R—$SO_3H$) and are available in various solvent systems, EWs and concentrations. Aquivion® PFSA grades have typically following monomer composition: TFE from 79 to 88 mol/mol % and SFVE from 21 to 13 mol/mol %.

The catalyst support can be obtained by cross-linking of the sulfonic fluorinated polymer, the cross-linking involving the backbone of the polymer. The polymers thus obtained are suitable both for use as ion conducting membranes in electrochemical cells as well as filtration membranes. Cross-linking of fluorinated polymers may also involve the sulfonyl fluoride functional group precursor to the sulfonic acid functional group has also been previously described.

The availability of a bifunctional catalyst in the process according to the present invention allows carrying out efficiently two reactions either in sequence or in a cooperative way in one-pot and using a single catalytic material: an acid-catalysed reaction (dehydration, esterification, isomerization, hydrolysis) and a metal-catalysed reduction. The advantages of the process of the present invention comprise the high purity of the final product, the lower number of operations required by the multistep preparation, the avoidance of any soluble acidic additive, the low energy inputs required, thus reducing time and costs (initial and operative), and the reduction of the process complexity (no need for purification and/or recovery of the intermediates).

Many prior art processes are currently carried out with homogeneous catalysts. The use of heterogeneous catalysis allows an easier catalyst separation and product purification.

In the process according to the invention, the hydrogenation and acid-catalysed dehydration/isomerization can take place simultaneously or in sequence, according to any order, i.e. the hydrogenation can precede or follow the dehydration/isomerization, depending on the specific reactivity of the substrate and of the intermediate chemical species involved, to yield ultimately the hydrogenated and dehydrated/isomerized compound.

The use of fluoropolymer-based catalyst according to the invention implies the contact of the ionomer structure with an aqueous or polar liquid having affinity with the ionic functional groups of the ionomer during the process of the invention. Generally, the larger the amount of ionic groups present in the chain, the better the efficiency in terms of catalyst activity in the process of the invention.

From this point of view, an important parameter is the equivalent weight of the ionomer. The amount of —$SO_3M$ functional groups in fluorinated polymer (P), measured in terms of acid groups —$SO_3H$, is correlated with the so-called "equivalent weight" (EW) of the polymer, that is the grams of fluorinated polymer per mole of acid functional groups (indicated as "eq").

The equivalent weight of the polymer (EW) can be determined by IR analysis. The lower the equivalent weight, the higher the percentage of sulphonic groups that are present in the chain. Therefore, ionomers having a low equivalent weight are desirable since they give a higher catalytic efficiency. The fluorinated polymer (P) typically has an equivalent weight of 500 g/eq or above, preferably not less than 450 g/eq or above, more preferably of 380 g/eq or above. The equivalent weight typically does not exceed 1600 g/eq, preferably it does not exceed 1200 g/eq, more preferably it does not exceed 900 or 1000 g/eq.

The fluorinated polymer (P) has a typical weight swelling ability of at least 0.5 mL of solvent absorbed, typically water, per 1 g of dry polymer at room temperature, it is available either in the form of powder of grain size in the range 60-500 mm (as determined via sieving techniques known to the person skilled in the art, e.g. ASTM 1921-12 or as macroreticular foams with pore size in the range 1-50 mm. The fluorinated polymer (P) allows for the anchoring of transition metal particles in amounts from 5 to 50 mole %, preferably 10 to 40 mole %, more preferably 20 to 30 mole %, with respect to the total moles of $SO_3H$ groups, depending on factors including the valence of the metal.

Within the context of the present invention the expression "at least one" when referred to a "fluorinated polymer" and/or to "metal particles" is intended to denote one or more than one polymer and/or to one or more type of metal particles. Mixtures of polymers and/or of metal particles can be advantageously used for the purposes of the invention.

The term "transition metal" indicates a metallic chemical element, whose atom has an incomplete d sub-shell, or which can give rise to cations with an incomplete d sub-shell, i.e. an element in the d-block of the periodic table, which includes groups 3 to 12 on the periodic table, namely first (3d) transition series (Sc—Zn), second (4d) transition series (Y—Cd) and third (5d) transition series (Lu—Hg).

Preferably, the metal particles on polymeric support (P) in the process of the invention comprise, or consist of, at least one metal, in non-charged or ionic form, selected from ruthenium, rhodium, platinum, palladium, copper, nickel, iridium, cobalt, osmium, rhenium, iron, and combinations thereof. More preferably, the metal is ruthenium, platinum, palladium or rhodium.

Within the context of the present invention, the term "particle" is intended to denote a mass of material that, from a geometrical point of view, has a definite three-dimensional volume and shape, characterized by three dimensions, wherein none of said dimensions exceed the remaining two other dimensions of more than 200%. Particles are generally not equidimensional, i.e. that are longer in one direction than in others. The shape of a particle can be notably expressed in terms of the sphericity $\Phi_s$, which is independent of particle size. The sphericity of a particle is the ratio of the surface-volume ratio of a sphere with equal volume as the particle and the surface-volume ratio of the particle. For a spherical particle of diameter $D_p$, $\Phi_s=1$; for a non-spherical particle, the sphericity is defined as $$\Phi_s=(6 \cdot v_p)/(D_p \cdot S_p)$$

wherein:
Dp is the equivalent diameter of particle;
Sp is the surface area of one particle;
vp is the volume of one particle.

The equivalent diameter is defined as the diameter of a sphere of equal volume. Dp is usually taken to be the nominal size based on screen analysis or microscopic analysis. The surface area is found from adsorption measurements or from the pressure drop in a bed of particles. The particles of polymer (P) have a sphericity $\Phi_s$ of preferably at least 0.6, more preferably at least 0.65, even more preferably at least 0.7. Good results have been obtained with particles having a $\Phi_s$ from 0.7 to 0.95.

As used herein, the term "particle size" refers to the equivalent diameter (Dp) of the metal particle, as determined by the general methods known to the person skilled in the art, such as screen analysis or microscopic analysis.

The metal particles in the process of the invention have particle size below 50 nm ("nanoparticles"), preferably below 20 nm, more preferably below 10 nm, even more preferably below 5 nm. In a particularly preferred embodiment, at least 90% of the metal particles in the catalyst according to the invention have size below 9 nm. The particle size is determined according to the methods routinely used and known to the person skilled in the art, such as via Transmission Electron Microscopy, X-ray Diffraction, Chemisorption, Small Angle X-ray Scattering.

It was found that the one-pot hydrogenation and acid-catalysed isomerisation or dehydration of a substrate (I) containing at least a C=C or C=O moiety to obtain a product (II) according to the present invention can be advantageously carried out at relatively low temperature and moderate pressure of hydrogen gas ($H_2$). Because relatively mild conditions can be used, the overall process of the invention is particularly cost-effective and scalable to industrial production using the routine procedure known to the person skilled in the art.

The process according to the invention can be carried out between 40 and 200° C. under a hydrogen pressure of 1 to 50 atm.

Preferably, in the process according to the invention, the step of reacting the substrate (I) with catalyst (III) in the presence of hydrogen is carried out at a temperature from 50 to 150° C., more preferably at temperatures below 100° C., even more preferably at room temperature and under hydrogen pressure below 50 atm, more preferably below 30 atm and even more preferably below 10 atm. The amount of catalyst (III) present in the reaction with the substrate (I) in the presence of hydrogen may vary according to the transition metal being used, to the chemical structure of the substrate, to the reaction conditions such as the nature of solvents, the pressure of hydrogen, the temperature etc., as known to the person skilled in the art of organic synthesis. Preferably, the amount of catalysts (III) is from 1:1 to 1:200 in weight with respect to the weight of substrate (I), corresponding to 1:100 to 1:10000 catalyst/substrate molar ratio range, based on 0.05 to 10% weight loading of the transition metal in catalyst (III).

It was found that the process according to the invention can be efficiently carried out in the presence of less than 1 mol % of the transition metal with respect to the molar amount of the substrate, whereas at least 5 mol % of the metal are generally required in the processes of the prior art. This is particularly advantageous in processes catalyzed by metals like platinum and palladium, wherein the amount of the precious metal to be used as a catalyst is a major component of the overall process cost.

Preferably, the amount of transition metal in catalyst (III) is less than 3% in weight, more preferably less than 2%, most preferably less than 1% in weight/total weight of the catalyst.

Advantageously, the step of reacting substrate (I) with hydrogen in the presence of catalyst (III) according to the process of the present invention can be carried out in the presence of water. Chemical transformations involving aqueous solvents are more environmentally-friendly and, generally, more cost-effective than processes carried out exclusively in organic solvents.

Preferably, in the process according to the present invention the solvent in the step of reacting substrate (I) with hydrogen in the presence of catalyst (III) comprises water, more preferably in at least 50% weight over the total weight of the solvent, even more preferably at least 80% or 90% weight over the weight of the solvent. Preferably, the process according to the present invention is carried out in a mixture of water and a water-miscible organic solvent including, but not limited to, water-methanol, water-ethanol, water-1,4-dioxane and water-acetone.

The one-pot hydrogenation and acid-catalysed isomerisation or dehydration of a substrate (I) containing at least a C=C or C=O moiety to obtain a product (II) according to the present invention can be advantageously used for the production of several advanced intermediates and complex chemicals.

In a preferred embodiment of the invention, levulinic acid (Ia) is converted into gamma-valerolactone (IIa) via reaction with catalyst (III) in the presence of hydrogen (Scheme 1).

It was found that (IIa) can be prepared according to the process of the present invention in good yield (>48%) and excellent selectivity also at low temperature (50° C.). By comparison, only 29% of (IIa) is obtained upon treatment of (Ia) at 50° C. under similar conditions, except that a catalyst comprising ruthenium nanoparticles supported on a non-fluorinated resin (Dowex® 50WX2, The Dow Chemical Company) is used instead of catalyst (III) on a fluoropolymer support, according to the present invention.

In addition, the intermediate gamma- hydroxyvaleric acid (HVA), frequently found as an impurity in (IIa) prepared according to the process of the prior art, is not present in (IIa) obtained according to the process of the present invention (content of HVA below detection limit of GC analysis).

Preferably, in the conversion of (Ia) to (IIa) according to the present invention the catalyst (III) comprises ruthenium, rhodium, palladium or platinum, more preferably ruthenium.

Preferably, in the conversion of (Ia) to (IIa) according to the present invention the catalyst (III) has an EW from 1100 to 500 g/eq, more preferably 1000 to 600 g/eq.

Preferably, in the conversion of (Ia) to (IIa) according to the present invention the solvent consists of water or comprises at least 80%, more preferably at least 90%, of water in weight with respect to the total weight of the solvent.

In another preferred embodiment of the invention, hemicellulose or cellulose (Ib) is converted into sorbitol (IIb) via reaction with catalyst (III) in the presence of hydrogen (Scheme 2).

Preferably, in the conversion of (Ib) to (IIb) according to the present invention the catalyst (III) comprises ruthenium, rhodium, palladium or platinum, more preferably ruthenium.

Sorbitol (IIb) is widely used in the food and pharmaceutical industries as low calorie sweetener, humectant, laxative and as a precursor to important substances such as surfactants and vitamin C. It is also a platform molecule for the preparation of several chemicals including ethylene glycol, propylene glycol, glycerol and isosorbide. At present, sorbitol is produced on commercial scale via enzymatic hydrolysis and catalytic hydrogenation of starch. Advantageously, the process of the present invention provides a route to sorbitol starting from hemicellulose or directly from cellulose, one of the most abundant organic compound in nature, that is inedible and can be easily obtained from low cost materials and from waste from several food/industrial processes.

In another preferred embodiment of the invention, xylose (Ic) is converted into levulinic acid, or an ester thereof (IIc) directly via reaction with catalyst (III) in the presence of hydrogen (Scheme 3).

Levulinic acid (Ia) and its esters (IIc) are important starting materials for the preparation of "green" solvents, as well as of a variety of building blocks and of biofuels. They are currently obtained on large scale by treatment of sucrose with concentrated HCl or sulphuric acid at high temperature. The process according to the present invention provides a one-pot route to (IIc) and (Ia) starting from (Ic) under mild conditions and in high yield. Alternatively, (IIc) and (Ia) can be prepared according to the process of the invention using furfural (via the intermediate furfuryl alcohol, which does not need to be isolated).

In another preferred embodiment of the invention, gamma-valerolactone (IIa) is converted into pentanoic acid (IId) via reaction with catalyst (III) in the presence of hydrogen (Scheme 4).

IId (Valeric acid or pentanoic acid) is an important advanced intermediate for several processes. Notably, by esterification, it provides alkyl valerate esters, which can be used as renewable fuels and in the food and perfumery industry.

In another preferred embodiment of the invention, glycerol (Ie) is converted into 1,2-propanediol (IIe) via reaction with catalyst (III) in the presence of hydrogen (Scheme 5).

Scheme 5

Scheme 7

Propylene glycol (1,2-propanediol, IIe) is industrially produced from propylene oxide at 150-200° C. in the presence of strong acids. The final product of such process contains 20% propylene glycol, 1.5% of dipropylene glycol and small amounts of other glycols. According to the process of the invention, (IIe) can be obtained in high yield and purity from a very common starting material, glycerol (Ie), that is obtained on a large scale from triglycerides found in fats and vegetable oils or as a by-product from the production of biodiesel from vegetable oils.

In another preferred embodiment of the invention, citronellal (If) is converted into menthol (IIf), via reaction with catalyst (III) in the presence of hydrogen (Scheme 6).

Methyl isobutyl ketone (IIg, MIBK) is the most important compound obtained from acetone, having a global production of several million kilogram per year, and is widely used for paints, resins and coatings, as well as in the chemical industry as a solvent in several processes. Commercial production of MIBK involves three steps and the drawbacks of the process are the use of separated reaction units, high temperatures and a large amount of waste. The process of the present invention provides a feasible one-pot route for the production of MIBK from acetone in high yield and purity using lower temperatures and producing less side-products with respect to the commercial processes.

In another preferred embodiment of the invention, glucose (Ih) is converted into 1,6-hexanediol (II'h) or 2,5-dimethylfuran (IIh) via reaction with the catalyst (III) in the presence of hydrogen (Scheme 8).

Scheme 6

Scheme 8

Menthol is the most demanded mint product, extensively used in flavouring, food, healthcare and pharmaceutical industry. Synthetic menthol (particularly the naturally occurring (−) isomer) is usually obtained via the Tagasako process, which is based on five steps starting from myrcene. The process of the present invention can be applied to citronellal, either racemic or isomerically enriched (R or S optical isomers) to obtain racemic, (+)- or (−)-menthol in high purity in one-pot in the presence of a non-chiral catalyst.

In another preferred embodiment of the invention, acetone (Ig) is converted into methyl isobutyl ketone (IIg), via reaction with catalyst (III) in the presence of hydrogen (Scheme 7).

The process of the invention provides access to 1,6-hexanediol, that is largely used in the production of nylon, polyesters and polyurethanes, starting from glucose, as an alternative to the current commercial process, which uses adipic acid as starting material. 2,5-dimethylfuran is used in the fuel industry as gasoline blender or octane booster and is a starting material for the manufacture of polyurethane foams or polyesters. Notably, the synthesis of 2,5-dimethylfuran from glucose according to the present invention is advantageous, because the starting material is affordable, easily obtainable from renewable sources and readily available on large scale.

The catalyst (III) can be prepared according to standard procedures known to the person skilled in the art. Non-limitative examples of procedures for the preparation of catalysts that can be used in the process of the present invention are disclosed in U.S. 2008/0003479 A (KONKUK UNIVERSITY) 3 Jan. 2008 and in WO 2013/162499 A (UNITED TECHNOLOGIES CORPORATION) 31 Oct. 2013.

In an embodiment, the present invention provides a solid composition comprising transition metal particles having particle size below 50 nm supported on a material comprising at least one fluorinated polymer (P) bearing —$SO_2X$ functional groups, wherein X is selected from X' and OM, X' being selected from the group consisting of F, Cl, Br, and I; and M is selected from the group consisting of H, an alkaline metal and $NH_4$, and (P) comprises recurring units deriving from tetrafluoroethylene (TFE) and a linear (i.e. non-branched) Sulfonyl Fluoride Vinyl Ether (SFVE).

Preferably, (P) comprises units deriving from a linear SFVE having formula $CF_2$=CF—O—$(CF_2)_n$—$SO_2F$, wherein n=2, 3 or 4, more preferably wherein n=2.

It was found that the composition according to the invention can be efficiently used as catalyst in one-pot hydrogenation and acid-catalysed isomerisation or dehydration of a substrate. Using the composition of the invention as a catalyst, less than 1 mol % of the transition metal with respect to the molar amount of the substrate is sufficient for the complete transformation with good to excellent selectivity under mild conditions, whereas at least 5 mol % of the metal and harsher conditions are generally required in the processes of the prior art, with a significant impact on the overall cost of the process.

Preferably, in the solid composition according to the invention, the transition metal particles have particle size below 20 nm, more preferably below 10 nm, even more preferably below 5 nm. In a particularly preferred embodiment, the size of at least 90% of the metal particles in the composition according to the invention is below 9 nm.

Preferably, in said solid composition the metal particles on the support (P) comprise, or consist of, at least one metal, in non-charged or ionic form, selected from ruthenium, rhodium, platinum, palladium, copper, nickel, iridium, cobalt, osmium, rhenium, iron, and combinations thereof, preferably wherein the metal is ruthenium, platinum, palladium or rhodium.

Preferably, in said solid composition, the polymer (P) has an equivalent weight of 500 g/eq or higher, preferably of 450 g/eq or higher, more preferably 380 g/eq or higher in grams of fluorinated polymer per mole of —$SO_3H$ functional groups.

Should the disclosure of any patents, patent applications, and publications which are incorporated herein by reference conflict with the description of the present application to the extent that it may render a term unclear, the present description shall take precedence.

The following examples are provided to illustrate typical embodiments of the invention and are not intended to limit its scope.

ESEM (Environmental Scanning Electron Microscopy) experiments were performed on a FEI Quanta 200 microscope operating at 25 keV accelerating voltage and equipped with an EDAX Energy Dispersive X-ray Spectrometer (EDS). TEM (Transmission Electron Microscopy) analyses were performed on a M12 PHILIPS instrument at 120 keV.

The metal loading in the catalysts and the amount of metal potentially leached in solution was determined by Inductively Coupled Plasma Atomic Emission Spectroscopy (ICP-OES) using a Varian 720ES instrument. In all examples no leaching of metal into the reaction solution was observed.

GC-analyses were performed on a Shimadzu GC 2010 chromatograph equipped with a flame ionization detector (FID) and a 30 m (0.25 mm ID, 0.25 µm FT) VF-WAXms column.

GC-MS analyses were performed on a Shimadzu QP5000 apparatus equipped with the same column.

Reactions under batch conditions were carried out using an inert autoclave equipped with a magnetic stirrer, a Teflon® inset and a pressure controller.

Example I. Preparation of Ru-Containing Catalyst

In a typical procedure, the dry polymeric material Aquivion® PFSA (250 mg, supplied by Solvay Specialty Polymers Italy, powder form, PSD 500-700 micron, composition: 79 mol/mol % TFE and 21 mol/mol % SFVE) was added to a flask containing a degassed brown solution of ruthenium(III) nitrosyl nitrate (229 mL of $Ru(NO)(NO_3)_x$ $(OH)_y$ nitric solution 1.5 wt % Ru, 0.036 mmol Ru, ratio Ru/sulfonic group=1/10.6) in deionised water (14.0 mL). The mixture was degassed with 3 cycles vacuum/nitrogen and then stirred at room temperature for 2 h using an orbital stirrer. The solid material, initially white, became immediately brown, while the solution color faded. The solid was then decanted and the colourless solution was removed by syringe. The solid was washed with degassed, deionised water (3×25 mL) before being dried under high vacuum at 60° C. overnight. The resulting metallated Aquivion® PFSA obtained as brown powder was stored under nitrogen.

Solid $NaBH_4$ was then added in excess (30:1) and under nitrogen to a flask containing the metallated Aquivion® PFSA resin obtained above and degassed water (10.0 mL). Bubbles appeared immediately while the resin changed colour from brown to black and the solution remained colourless. After 2 h at room temperature and 250 rpm orbital stirring, the solid was decanted and was washed with degassed water (4×25 mL), before being dried under high vacuum at 60° C. overnight. The resulting resin obtained as black powder was stored under nitrogen.

A ruthenium loading of 1.16 wt % was measured from ICP-OES analysis, corresponding to 80.0% metal uptake.

Example II. Preparation of Rh-Containing Catalyst

A degassed orange solution of $[Rh(NBD)_2]BF_4$ (32.9 mg, 0.088 mmol, ratio $SO_3H$/Rh=10.5) in THF (17.0 mL) was added under nitrogen via syringe to a degassed suspension of (600 mg) in THF (17.0 mL). The mixture was stirred at room temperature for 24 h using an orbital stirrer. The resulting solid material was decanted, washed with THF (3×25 mL) and diethyl ether (20 mL) before being dried under high vacuum overnight. The metal-containing Aquivion® orange powder thus obtained was stored under nitrogen.

Solid $NaBH_4$ (100 mg) was then added under nitrogen to a degassed suspension of the metal-containing resin in water (15 mL). The mixture was allowed to react for 24 h with orbital stirring. After that time, the solid was decanted, washed with degassed water (4×25 mL), and dried under high vacuum at 50° C. overnight. The resulting product obtained as black powder was stored under nitrogen.

A rhodium loading of 1.41 wt % was measured from ICP-OES analysis, corresponding to 95.3% metal uptake.

Example III. Preparation of Pd-Containing Catalyst

In a typical procedure, a degassed brownish solution of $Pd(NO_3)_2$ (23.4 mg, 0.088 mmol, ratio $SO_3H$/Rh=10.5) in water (17.0 mL) was added under nitrogen via syringe to a degassed suspension of Aquivion® PFSA (600 mg) in water (17.0 mL). The mixture was stirred at room temperature for 24 h using an orbital stirrer. The resulting solid material was decanted and washed with degassed water (3×25 mL). Water (25 mL) was then added under nitrogen and $H_2$ was bubbled through the suspension at 1 bar for 2 h with stirring. The solid obtained was washed with degassed water (2×25 mL) before being dried under high vacuum at 50° C. overnight. The resulting resin obtained as black powder was stored under nitrogen.

A palladium loading of 1.33 wt % was measured from ICP-OES analysis, corresponding to 86.9% metal uptake.

Example IV. Preparation of Pt-Containing Catalyst

Dry polymeric material Aquivion® PFSA (250 mg) was added to a flask containing a degassed solution of [Pt (NH$_3$)$_4$](NO$_3$)$_2$ (14.1 mg, 0.036 mmol Pt, ratio Pt/sulfonic groups=1/10.6) in deionised water (14.0 mL). The mixture was degassed with 3 cycles vacuum/nitrogen and then stirred at room temperature for 2 h using an orbital stirrer. After that time, the solid was decanted and the solution was removed by syringe. The solid was washed with degassed, deionised water (3×25 mL) before being dried under high vacuum at 60° C. overnight. The resulting metallated Aquivion® obtained as white powder was stored under nitrogen.

Solid NaBH$_4$ was then added in excess (30:1) and under nitrogen to a flask containing the metallated Aquivion® PFSA resin and degassed water (10.0 mL). Bubbles appeared immediately, the resin changed colour from white to grey and the solution remained colourless. After 2 h at room temperature and 250 rpm orbital stirring, the solid was decanted, washed with degassed water (4×25 mL) and then dried under high vacuum at 60° C. overnight. The resulting resin obtained as grey powder was stored under nitrogen.

A platinum loading of 2.53 wt % was measured from ICP-OES analysis, corresponding to 91.7% metal uptake.

Catalytic Reactions

Example V. Direct Catalytic Conversion of Levulinic Acid (Ia) to Gamma-Valerolactone (IIa)

The supported catalyst of example I (60 mg, 1.16 wt % Ru, 0.007 mmol of ruthenium), was placed under nitrogen into a metal-free autoclave. A degassed solution of levulinic acid (0.43 M, 2.15 mmol) in deionized water (5.0 mL) was transferred under nitrogen via a Teflon tube into the autoclave. Nitrogen was replaced by hydrogen with three cycles pressurization/depressurization. The autoclave was finally charged with 5 bar pressure of hydrogen, stirred at 150 rpm using a mechanical stirrer and heated up to 70° C. using an oil bath. After 4 hours, the reactor was cooled down to room temperature, depressurized and the solution was completely removed using a gas-tight syringe. A sample of this solution was used for GC and HPLC (product yield), GC-MS and NMR (product identification) and ICP-OES analysis (metal leaching). The only product detected was gamma-valerolactone with a yield of 79.8%, corresponding to a turnover frequency of 62 h$^{-1}$ (moles of substrate converted/moles metal×h). No traces of gamma-hydroxyvaleric acid (HVA) were observed.

Example VI. Direct Catalytic Conversion of Levulinic Acid (Ia) to Gamma-Valerolactone (IIa)

The procedure of example V was repeated, with the only difference that the autoclave was heated to 50° C., instead of 70° C., using an oil bath. The only product obtained after 4 h was gamma-valerolactone with a yield of 48.5%, corresponding to a turnover frequency of 38 h$^{-1}$. No traces of gamma-hydroxyvaleric acid (HVA) were observed.

Comparative Example I. Catalytic Conversion of Levulinic Acid (Ia) to Gamma-Valerolactone (IIa) Using a Non-Fluorinated Catalyst The procedure of example VI was repeated, using Ruthenium supported on a non-fluorinated catalyst (Ru supported on DOWEX® 50WX2-100 resin, obtained by a procedure comprising stirring a solution of RuCl$_3$ in water in the presence of the resin for 4 days, reference: MORENO-MARRODAN, CARMEN, et al. "Energy efficient continuous production of gamma-valerolactone by bifunctional metal/acid catalyst in one pot". *Green Chem.* 2014, vol. 16, p. 3434.) Gamma-valerolactone was obtained as the only product after 4 h AT 50° C. with a yield of 29.3%, corresponding to a turnover frequency of 30.5 h$^{-1}$.

Example VII. Direct Catalytic Conversion (R)-(+)-Citronellal (If) to Menthol (IIf)

The supported catalyst of example III (60 mg, 1.33 wt % Pd, 0.007 mmol of palladium), was placed under nitrogen into a metal-free autoclave. Neat (A)-(+)-citronellal (133.0 mg, 0.86 mmol) was then added under nitrogen. Degassed and deionized water (9.0 mL) was transferred under nitrogen via a Teflon tube into the autoclave. Nitrogen was replaced by hydrogen via three cycles of pressurization/depressurization. The autoclave was finally charged with 10 bar pressure of hydrogen, stirred at 150 rpm using a mechanical stirrer and heated up to 80° C. using an oil bath. After 48 hours, the reactor was cooled o room temperature, depressurized and the solution was completely removed using a gas-tight syringe. A sample of the solution thus obtained was used for GC and HPLC (product yield), GC-MS and NMR (product identification) and ICP-OES analysis (no metal leaching was observed). The only product detected was (−)-menthol with 100.0% conversion of the starting citronellal. No traces of isopulegol or of any other by-product were observed.

The invention claimed is:

1. A process for the one-pot hydrogenation and acid-catalysed isomerisation or dehydration of a substrate (I) containing at least a C=C, a C=O, an acetal, a 1,2-diol or a hemiacetal moiety to obtain a product (II), wherein said process comprises reacting the substrate (I) with hydrogen (H$_2$) in the presence of a catalyst (III), said catalyst comprising transition metal particles having particle size below 50 nm supported on a material comprising at least one fluorinated polymer (P), wherein polymer (P) bears —SO$_2$X functional groups, X being selected from X' and OM, X' being selected from the group consisting of F, Cl, Br, and I; and M being selected from the group consisting of H, an alkaline metal and NH$_4$.

2. The process according to claim 1, wherein the transition metal particles in the catalyst consist of at least one transition metal, in non-charged or ionic form, selected from ruthenium, rhodium, platinum, palladium, copper, nickel, iridium, cobalt, osmium, rhenium, iron, and combinations thereof.

3. The process according to claim 1, wherein the step of reacting the substrate (I) with catalyst (III) is carried out at a temperature from 50 to 150° C.

4. The process according to claim 1, wherein levulinic acid (Ia) is converted into gamma-valerolactone (IIa), hemicellulose or cellulose (Ib) is converted into sorbitol (IIb), xylose (Ic) is converted into levulinic acid or an ester thereof (IIc), gamma-valerolactone (IIa) is converted into pentanoic acid (IId), glycerol (Ie) is converted into 1,2-propanediol (IIe), citronellal (If) is converted into menthol (IIf), acetone (Ig) is converted into methyl isobutyl ketone (IIg), or glucose (Ih) is converted into 1,6-hexanediol or 2,5-dimethylfuran (IIh).

5. The process according to claim 4, wherein the substrate (I) is levulinic acid (Ia) and the product (II) is gamma-valerolactone (IIa).

6. The process according to claim 1, wherein the a least one fluorinated polymer bearing —$SO_2X$ functional groups comprises recurring units derived from at least one ethylenically unsaturated fluorinated monomer containing at least one —$SO_2X'$ functional group (monomer A) and recurring units derived from at least one ethylenically unsaturated fluorinated monomer (monomer B).

7. The process according to claim 6, wherein the a least one fluorinated polymer (P) comprises:
   recurring units derived from at least a monomer (A), wherein monomer (A) is selected from:
   sulfonyl halide fluoroolefins of formula: $CF_2=CF(CF_2)_pSO_2X'$ wherein p is an integer between 0 and 10;
   sulfonyl halide fluorovinylethers of formula: $CF_2=CF-O-(CF_2)_mSO_2X'$ wherein m is an integer between 1 and 10;
   sulfonyl halide fluoroalkoxyvinyl ethers of formula: $CF_2=CF-(OCF_2CF(R_{F1}))_w-O-CF_2(CF(R_{F2}))_ySO_2X'$ wherein w is an integer between 0 and 2, $R_{F1}$ and $R_{F2}$, equal or different from each other, are independently F, Cl or a $C_1$-$C_{10}$ fluoroalkyl group, optionally substituted with one or more ether oxygens, y is an integer between 0 and 6;
   sulfonyl halide aromatic fluoroolefins of formula $CF_2=CF-Ar-SO_2X'$ wherein Ar is a $C_5$-$C_{15}$ aromatic or heteroaromatic substituent; and
   recurring units derived from at least a monomer (B), wherein monomer (B) is selected from
   $C_2$-$C_8$ fluoroolefins;
   $C_2$-$C_8$ chloro- and/or bromo- and/or iodo-fluoroolefins;
   fluoroalkylvinylethers of formula $CF_2=CFOR_{f1}$, wherein $R_{f1}$ is a $C_1$-$C_6$ fluoroalkyl;
   fluoro-oxyalkylvinylethers of formula $CF_2=CFOR_{O1}$, wherein $R_{O1}$ is a $C_1$-$C_{12}$ fluoro-oxyalkyl having one or more ether groups; fluoroalkyl-methoxy-vinylethers of formula $CF_2=CFOCF_2OR_{f2}$ in which $R_{f2}$ is a $C_1$-$C_6$ fluoroalkyl or a $C_1$-$C_6$ fluorooxyalkyl having one or more ether groups;
   fluorodioxoles, of formula:

wherein each of $R_{f3}$, $R_{f4}$, $R_{f5}$, $R_{f6}$, equal or different each other, is independently a fluorine atom, a $C_1$-$C_6$ fluoroalkyl, optionally comprising one or more oxygen atom.

8. The process of claim 7, wherein monomer (A) selected from the group of the fluorovinylethers of formula $CF_2=CF-O-(CF_2)_m-SO_2F$, wherein m is an integer between 1 and 6, and/or monomer (B) is selected from:
   $C_3$-$C_8$ fluoroolefins;
   chloro- and/or bromo- and/or iodo-$C_2$-$C_6$ fluoroolefins;
   fluoroalkylvinylethers of formula $CF_2=CFOR_{f1}$ wherein $R_{f1}$ is a $C_1$-$C_6$ fluoroalkyl;
   fluoro-oxyalkyl- vinylethers of formula $CF_2=CFOR_{O1}$, wherein $R_{O1}$ is a $C_1$-$C_{12}$ fluorooxyalkyl having one or more ether groups.

9. The process of claim 8, wherein monomer (A) is $CF_2=CFOCF_2CF_2-SO_2F$ (perfluoro-5-sulfonylfluoride-3-oxa-1-pentene) and/or monomer (B) is tetrafluoroethylene.

10. The process of claim 1, wherein the step of reacting the substrate (I) with hydrogen ($H_2$) in the presence of a catalyst (III) is carried out in a solvent system comprising water.

11. Use of a catalyst (III) comprising transition metal particles having particle size below 50 nm supported on a material comprising at least one fluorinated polymer (P), wherein polymer (P) bears —$SO_2X$ functional groups, X being selected from X' and OM, X' being selected from the group consisting of F, Cl, Br, and I; and M being selected from the group consisting of H, an alkaline metal and $NH_4$, in the one-pot hydrogenation and acid-catalysed isomerisation or dehydration of a substrate (I) containing at least a C=C or C=O moiety to obtain a product (II), wherein said process comprises reacting the substrate with hydrogen ($H_2$) in the presence of catalyst (III).

12. A solid composition comprising transition metal particles having particle size below 50 nm supported on a material comprising at least one fluorinated polymer (P), wherein polymer (P) bears —$SO_2X$ functional groups, X being selected from X' and OM, X' being selected from the group consisting of F, Cl, Br, and I; and M being selected from the group consisting of H, an alkaline metal and $NH_4$, and (P) comprises recurring units derived from tetrafluoroethylene (TFE) and a linear Sulfonyl Fluoride Vinyl Ether (SFVE).

13. The solid composition according to claim 12, wherein the transition metal particles have a particle size below 10 nm.

14. The solid composition according to claim 12, wherein the metal particles on the support (P) comprise at least one metal, in non-charged or ionic form, selected from ruthenium, rhodium, platinum, palladium, copper, nickel, iridium, cobalt, osmium, rhenium, iron, and combinations thereof.

15. The solid composition according to claim 12, wherein the polymer (P) has an equivalent weight of 500 g/eq or higher in grams of fluorinated polymer per mole of —$SO_3H$ functional groups.

16. The solid composition according to claim 14, wherein the metal particles on the support (P) consist of at least one metal, in non-charged or ionic form, selected from ruthenium, platinum, palladium and rhodium.

17. The solid composition according to claim 15, wherein the polymer (P) has an equivalent weight of 380 g/eq or higher in grams of fluorinated polymer per mole of —$SO_3H$ functional groups.

18. The process according to claim 7, wherein monomer (A) is selected from:
   sulfonyl halide fluoroolefins of formula: $CF_2=CF(CF_2)_pSO_2X'$ wherein p is equal to 2 or 3 and X' is F;
   sulfonyl halide fluorovinylethers of formula: $CF_2=CF-O-(CF_2)_mSO_2X'$ wherein m equals 2 and X' is F;

sulfonyl halide fluoroalkoxyvinyl ethers of formula: $CF_2=CF-(OCF_2CF(R_{F1}))_w-O-CF_2(CF(R_{F2}))_y$-$SO_2X'$ wherein w is 1, $R_{F1}$ is $-CF_3$, y is 1, $R_{F2}$ is F, and X' is F;

sulfonyl halide aromatic fluoroolefins of formula $CF_2=CF-Ar-SO_2X'$ wherein Ar is a $C_5$-$C_{15}$ aromatic or heteroaromatic substituent and X' is F.

19. The process according to claim 8, wherein monomer (B) is selected from:

tetrafluoroethylene, and/or hexafluoropropylene;
chlorotrifluoroethylene and/or bromotrifluoroethylene;
fluoroalkylvinylethers of formula $CF_2=CFOR_{f1}$ wherein $R_{f1}$ is $-CF_3$, $-C_2F_5$, or $-C_3F_7$; and
fluoro-oxyalkyl-vinylethers of formula $CF_2=CFOR_{O1}$, wherein $R_{O1}$ is perfluoro-2-propoxy-propyl.

* * * * *